United States Patent
Burnett et al.

[11] Patent Number: 5,404,100
[45] Date of Patent: Apr. 4, 1995

[54] METHOD OF QUANTIFYING WEAR PARTICLES IN A LUBRICANT SAMPLE

[75] Inventors: Kenneth F. Burnett, Reading; David B. Jones, Swansea; Mervin H. Jones, Swansea, all of United Kingdom

[73] Assignees: University College of Swansea, West Glamorgan; Analex Limited, Reading, both of United Kingdom

[21] Appl. No.: 984,710

[22] Filed: Dec. 3, 1992

[51] Int. Cl.$^6$ .................. G01N 27/74; G01R 33/12
[52] U.S. Cl. .................. 324/204; 324/202; 324/207.22; 340/631; 73/61.42
[58] Field of Search .......... 324/204, 71.1, 71.4, 324/228, 234, 239, 202, 207.22; 73/864.34, 53.01, 53.05, 61.42, 61.59, 64.56; 340/627, 631

[56] References Cited
U.S. PATENT DOCUMENTS 4,548,088 10/1985 Hood, Jr. .................. 73/864.34
4,930,360 6/1990 Tan .................. 73/864.34

FOREIGN PATENT DOCUMENTS

WO8504715 10/1985 WIPO .

*Primary Examiner*—Kenneth A. Wieder
*Assistant Examiner*—Jay M. Patidar
*Attorney, Agent, or Firm*—Synnestvedt & Lechner

[57] ABSTRACT

Wear particle monitoring is carried out on samples of a lubricating oil extracted from lubricated equipment together with the naturally appearing burden of ferromagnetic particles. The extracted sample is collected in a bottle to a depth sufficient to exceed the flux field of a sensing coil to which the bottle is subsequently applied whereby the numerical value (PQ value) assigned to the particle burden is substantially insensitive of the volume of liquid in the bottle. From time dependent measurements information as to the size of the particles in the burden can be obtained.

7 Claims, 4 Drawing Sheets

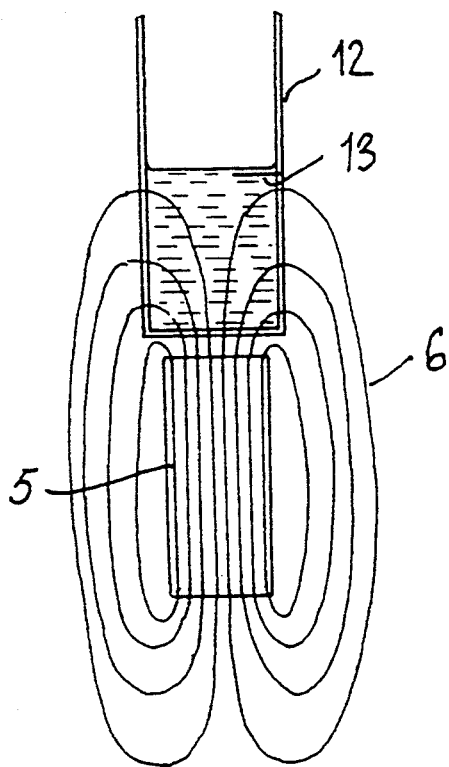
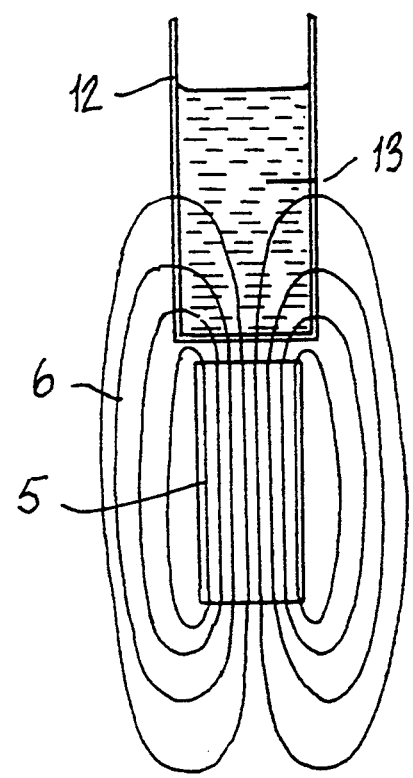
FIG. 3  FIG. 4
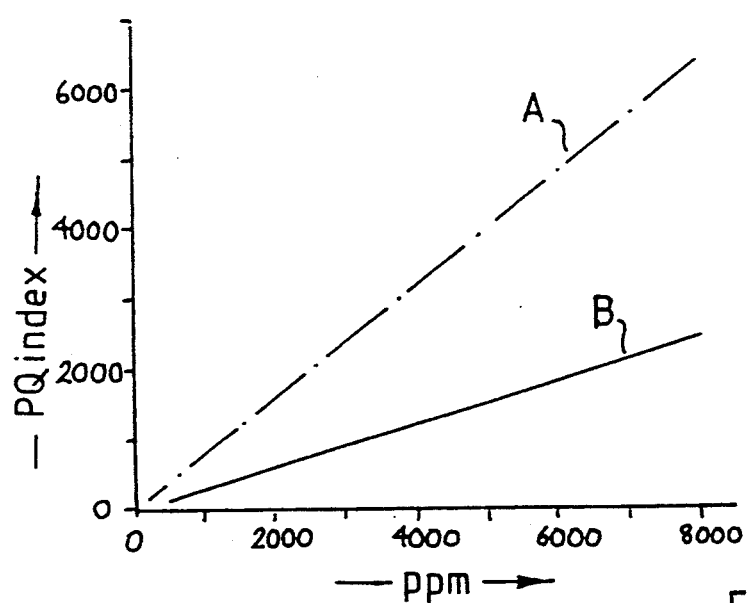
FIG. 5

METHOD OF QUANTIFYING WEAR PARTICLES IN A LUBRICANT SAMPLE

TECHNICAL FIELD

This invention relates, in general, to a technique for monitoring for increasing wear in moving parts of machinery by monitoring the amount of ferromagnetic material suspended in a sample of lubricant taken from the machinery.

DISCUSSION OF PRIOR ART

It is known to monitor the burden of wear debris suspended in lubricating oil by separating the suspended particles from the oil sample e.g. by using a rotary particle depositor and quantifying the amount of particulate matter contained in a given sample volume of oil. Electronic equipment permitting routine evaluation of oil samples taken from machinery is known, two particular examples being the PQ2000, disclosed for example in GB-A-2160655 and WO-A-85/04715, and the PQ90, a device developed and manufactured by the Tribology Centre of the University of Swansea and distributed by Analex Limited.

In the use of these known devices, the wear particles are either separated from the sample of lubricating oil and deposited on a glass slide using, for example, a rotary particle depositor described in GB-A-2172220 or a measured volume of lubricating oil with its burden of wear particles is contained in a small sample pot as described in WO-A-85/04715. In the known particle quantifying (PQ) devices the electronic equipment senses changes in the strength of a magnetic field caused by the presence of ferromagnetic wear material in that field, and assigns a numerical value to the level of change so determined. Such equipment has proved to be of significant commercial importance, particularly in providing trend analysis data for condition monitoring of oil-containing compartments. The degree of mechanical wear of machinery lubricated with oil from such compartments can often be determined from a knowledge of the amount of ferromagnetic material in the sample of the oil and, indeed, the onset of catastrophic wear is often associated with an increase in the number of large particles appearing in the oil. The PQ devices are particularly sensitive to the presence of such large particles and as a result such apparatus is being increasingly used in preventive maintenance programmes.

One of the features of the PQ90 device currently available is the speed at which samples may be measured and data presented and this speed is partly due to the fact that measurements can be made directly on extracted samples of oil without the need to separately deposit the burden of particles contained in the oil samples contain and wash away the suspending oil. Nonetheless, the existing recommended sample procedure requires that for each test a fixed volume of oil is pipetted into a sample pot and allowed to stand for a fixed period of time prior to measurement. The pipetted volumes are typically 1 to 3 mls and standing times would typically be 1 to 2 minutes. These restrictions mean that most measurements on PQ90 devices to date have been made in laboratory environments where parameters such as small volumes and short dwell times can be strictly controlled. It has been felt for some time that it would be of considerable advantage to the commercial value of a PQ90 device if it were possible for it to be used easily in the field where the oil samples are extracted and the data is of most immediate value. We have jointly developed a method which allows an oil sample to be presented directly to a PQ90 device without the need to measure a fixed volume of oil and without the need to introduce timed delays.

In addition, the method of this invention offers the capability of obtaining important information concerning the particle size distribution of ferromagnetic wear debris contained within the sample, by monitoring the change of PQ index with time.

SUMMARY OF THE INVENTION

According to one aspect of the invention a method of monitoring a sample of lubricating oil to quantify the ferromagnetic particle burden contained therein comprises extracting a sample of oil with its particle burden from a use point of the oil, placing that sample in a container to fill the container at least to a given depth and placing the container and its charge of oil in the magnetic flux field of a sensing electromagnetic coil which flux field does not effectively exceed the said depth of the oil in the container.

By the simple expedient of arranging the PQ device so that the effective flux field extends over a part only of the lower part of the available depth in the container, the need for providing accurate volumes within the container is instantly avoided, the sole requirement being that there is at least enough oil in the container to exceed the upper extent of the effective flux field passing through the container.

In accordance with a preferred arrangement, a sample of oil is drawn from an oil-containing compartment of equipment of interest either whilst the equipment is operating or immediately after it has ceased operating, to ensure that the debris material is in suspension and that the sample taken is representative of the lubricant circulating through the machinery lubricated from the compartment. The sample can typically be withdrawn using a suction sampling pump which applies suction to the downstream end of a length of plastics tube contained in a screw-capped sample bottle threaded onto the pump body, the upstream end of said length being passed into the oil-containing compartment so that the extracted oil sample is transferred directly from the compartment to the bottle along the tube without contacting the pump. This general method of sampling is known to be standard practice within condition monitoring programmes and a suitable pump is described in U.S. Pat. No. 4548088. A typical sample bottle will have a volume of 35 mls and an outside diameter of 30 mm but this should not be looked upon as a restriction and bottles of alternative sizes could be used. Desirably the material of the bottle should not affect the flux field to any significant extent.

The volume of oil sucked from the compartment into the bottle is not important provided a sufficient volume is taken to exceed a minimum depth of oil in the bottle. Typically 10 mls of oil would be needed, but samples of two or more times this volume do not appear to adversely affect the quantification figure obtained. When a sufficient volume of oil has been transferred to the bottle, this can be capped, shaken and brought to the sensing head of a PQ device for quantification. The resulting PQ index is displayed and may be stored in a memory for subsequent analysis. Thus a sample which gives a high PQ index, indicating a possible wear condition that needs investigation, may then be sent in the same sample bottle in which it was collected for more detailed investigation without any further sampling or contact with the machinery in question. If the value of the PQ index as measured in the bottle causes concern then the monitored machine can be stopped on the basis of this evidence and prior to a more detailed examination of the sample.

In addition, samples which give a high PQ index may be evaluated further on site and immediately following the initial measurement, to give important information concerning the particle size distribution. Consecutive measurements on the PQ90 will show an increase in PQ index with time as a result of particles settling in the bottle. A rapid increase in PQ index with time will indicate the presence of large particles which is often indicative of the onset of catastrophic wear conditions. A slow increase in the PQ index with time will usually indicate the presence of smaller particles. Measurements taken on the same, undisturbed sample at set intervals following the initial measurement can thus give valuable information concerning the ratio of large to small particles within the oil sample. Such a ratio is now seen to be an important factor within an oil condition monitoring programme in the determination of the consequent action required in the face of the data obtained.

Oil samples which are not immediately offered to a PQ device can nonetheless be quantified for wear particle content. These samples should, however, be well shaken prior to measurement (to ensure there is a substantially uniform dispersion of wear particles throughout the contained volume) and if the oil has thickened, warmed to the point where ready dispersion of the wear particle burden throughout the liquid sample will be obtained on shaking. With many commercially available lubricants, a temperature of 60° C. is satisfactory to ensure adequate low viscosity for shaking and shaking times of between 30 and 60 seconds would normally be adequate.

BRIEF DESCRIPTION OF THE DRAWINGS

The invention will now be further described, by way of example, with reference to the accompanying drawings, in which FIGS. 3 and 4 illustrate, schematically, the way in which sample volume does not significantly affect the quantification process, FIG. 5 is a graph of PQ index against particle concentration (ppm iron) for both the existing sample method (hereafter referred to as the "pot method") and the method of this invention (hereinafter referred to as the "bottle method"), and shows a sharp increase in sensitivity for the method of this invention.

DESCRIPTION OF PREFERRED EMBODIMENT

Figure 1:
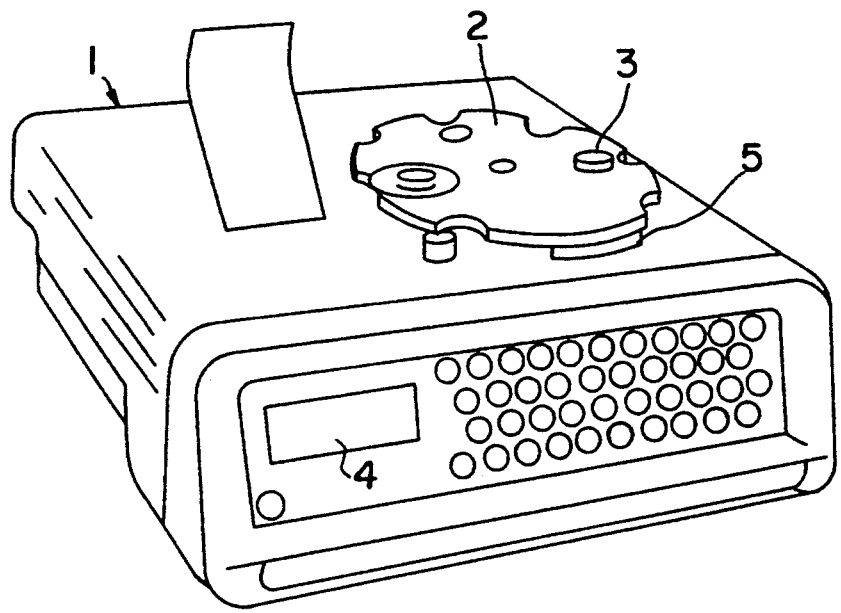
FIG. 1 is a schematic representation of a PQ device used in a prior art manner.

Referring to the drawings, FIG. 1 shows a PQ device 1 provided with a rotatable turntable 2 which incorporates a ring of apertures in which sample pots 3 can be located. Each sample pot contains a metered volume of oil taken from a machine under test, these pots being conveyed one by one above a sensing head (schematically indicated at 5), the electronic components of the PQ90 device 1 quantifying each sample in turn and displaying the number so obtained on a read-out panel 4.

The samples in the pots 3 have to be carefully prepared with regard to volume and a difference in PQ index will be obtained with different volumes of oil, or if the quantification is taken too soon after the sample is placed in the pot 3.

Figure 2:
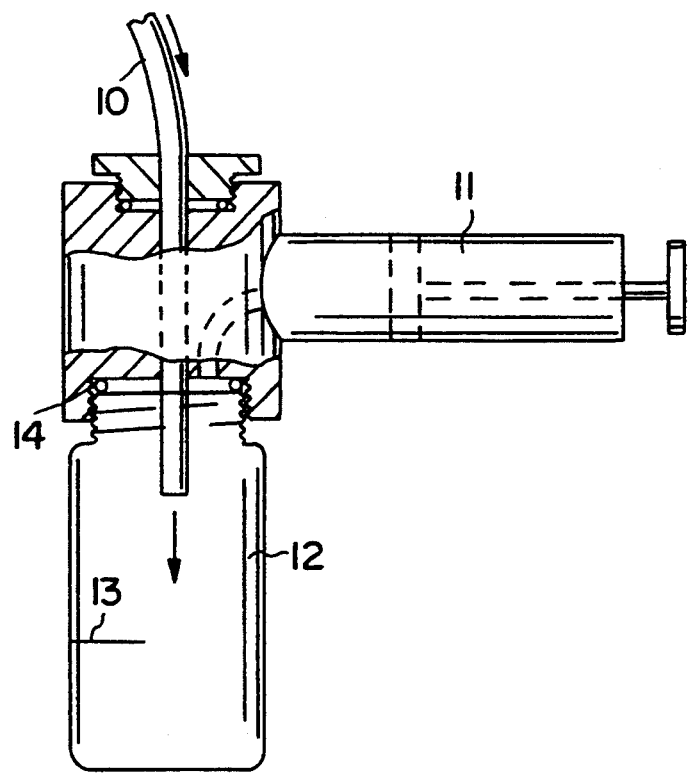
FIG. 2 is a schematic view of modified extraction equipment for obtaining samples for burden quantification using the method of this invention.

FIG. 2 shows equipment for extracting oil and passing it into containers for use in the bottle method in accordance with the present invention. A tube of plastics material 10 leads from an oil-filled compartment (not shown) of oil lubricated machinery under test and a manually operated vacuum pump 11 is sealed to the tube 10 and supports a screw-threaded bottle 12 via a vacuum tight thread adaptor 14. Using the pump 11, a pressure reduction is created in the bottle 12 which draws a volume of oil into the bottle which is at least more than that required to reach a line 13 marked on the bottle 12. The oil is extracted from the machinery under conditions in which the sample taken is typical of the oil circulating in the machinery during its normal operation.

By unscrewing the bottle 12 from the pump 11 after at least the required sample volume has been passed into it and then capping it with a screw cap matching the thread on the top of the bottle, a sample is immediately available for quantifying on a modified PQ90 device which has the turntable 2 adapted to receive the larger bottles 12.

The quantified reading from an oil sample using the bottle method is not dependent on the level of the sample in the bottle provided the latter exceeds the depth set by the line 13. The level of sample in a pot 3 using the prior art method would be well below the depth set by line 13 and hence the need for accuracy in the volume of sample dispensed to the pot when operating in the known manner.

This property of a PQ90 when used for measurements in accordance with this invention is illustrated in general terms by consideration of FIGS. 3 and 4. FIG. 3 shows the sensing head 5 and part of the flux field 6 created thereby. The strength of the flux field is affected by a sample of oil supporting a given concentration of ferromagnetic particles, FIG. 3 showing the flux field when the oil level just reaches the line 13 and FIG. 4 showing the flux field when the oil level is above the line 13. Since there is significantly no flux above the level of the line 13, closely similar readings are obtained with the samples shown in FIG. 3 and FIG. 4. This removal of the dependence on the maximum volume of the sample is a significant commercial advantage for the bottle method herein described.

The sensor head of the modified PQ90 is desirably located flush with the top face of the instrument cabinet. There are no other restrictions above the sensor head to limit the height of the bottle containing the oil sample being measured.

FIG. 5 shows the relationship between concentration, in ppm of 7 to 8 micron spherical ferrous particles, forming the burden in an oil of viscosity 14 CST at 40° C. Graph A is the PQ index measured by the bottle method with 20 ml of oil and graph B the PQ index measured using a pot containing 1 ml of oil. An approximately three-fold increase in sensitivity of the bottle method over the pot method can be seen to exist. Good linearity exists over the range 500 to 8000 ppm with both graph A and graph B.

Figure 6:
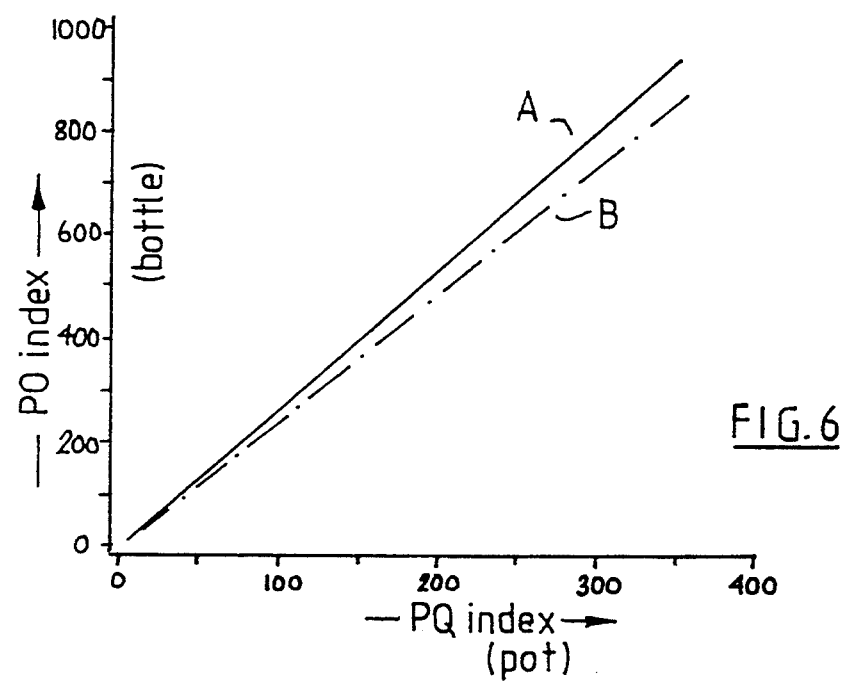
FIG. 6 is a graph of PQ index for samples measured in pots against PQ index for the same samples measured in quarter full and three-quarter full bottles, and indicates the insensitivity of the bottle method with respect to volume.

FIG. 6 shows the effect of volume of sample on the PQ index determined by the bottle method. Graph A in FIG. 6 relates to bottles containing 22.5 ml (¾ full) of a wide range of samples with different particle burdens and graph B relates to bottles containing 7.5 ml of the same range of samples (bottle ¼ full) and both are plotted against PQ index readings taken for the same range of samples but using 1 ml of oil in pots.

Figure 7:
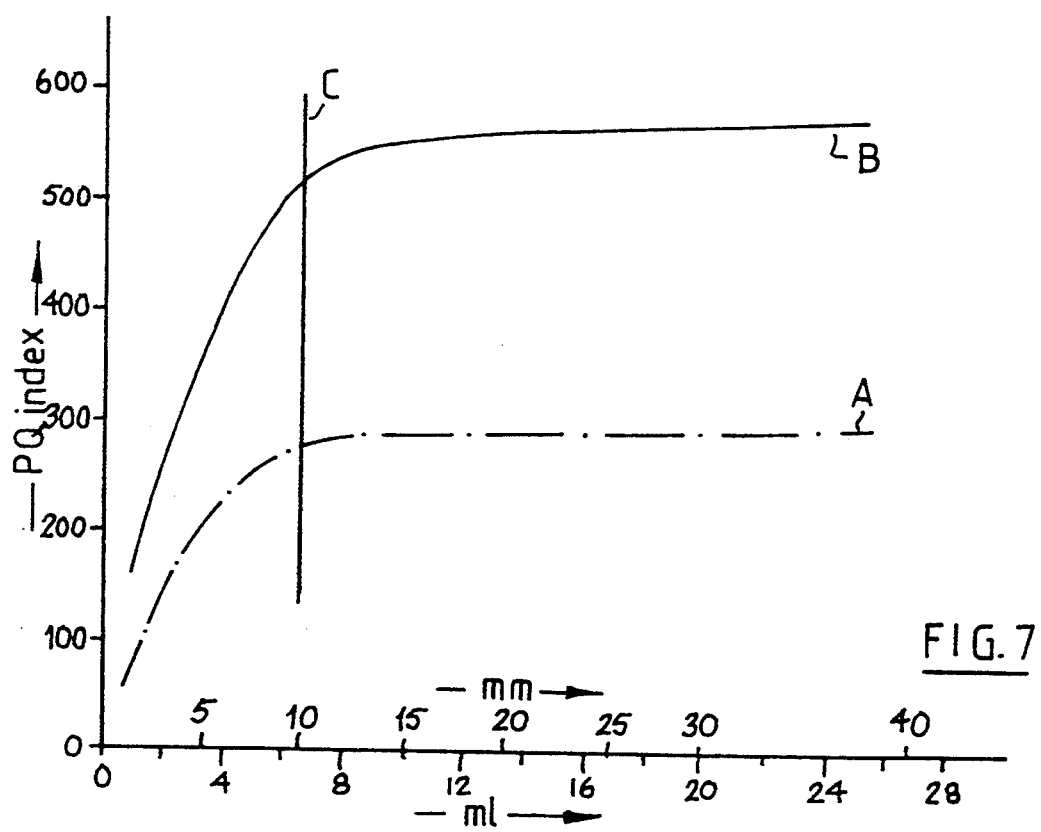
FIG. 7 is a graph of PQ index for two different samples measured as a function of the volume of the samples in the bottles.

FIG. 7 shows a graph of the PQ readings recorded on the PQ device of FIG. 1 using the bottle method with increasing volumes of oil in the bottle. Graph A is for a particle burden of 500 ppm and graph B for a burden of 1000 ppm, both graphs applying to spherical particles of sizes between 4 and 5 microns diameter. Also marked on the abscissa are the depth readings in the bottles corresponding to the quoted volumes. It will be noted that for both burden samples the PQ reading rises with increasing depth until a depth of some 10 mm when the PQ reading becomes substantially insensitive of increasing depth. Thus, the effective height of the magnetic flux field is determined. Accordingly the method of this invention involves operating to the right of the line C in FIG. 7 (e.g. at 10 mm or above).

Figure 8:
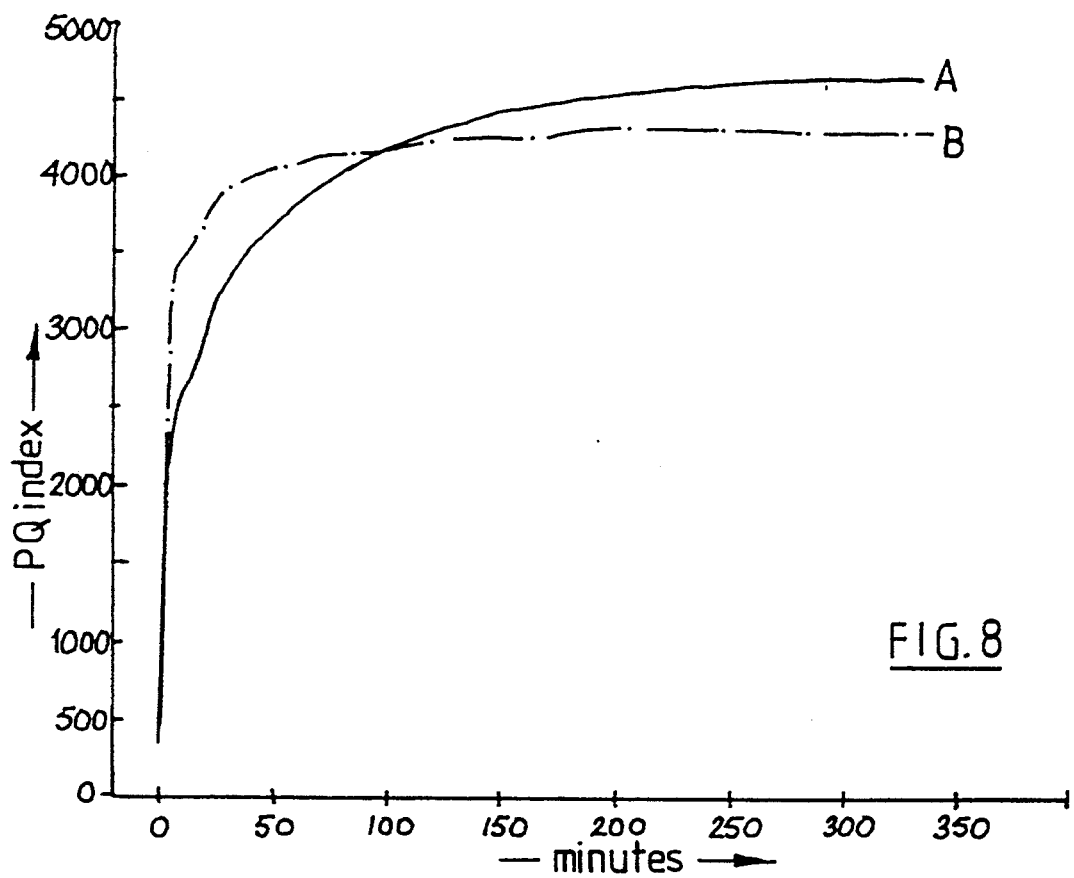
FIGS. 8 and 9 are two graphs of PQ index as a function of time each for two different samples in bottles.
Figure 9:
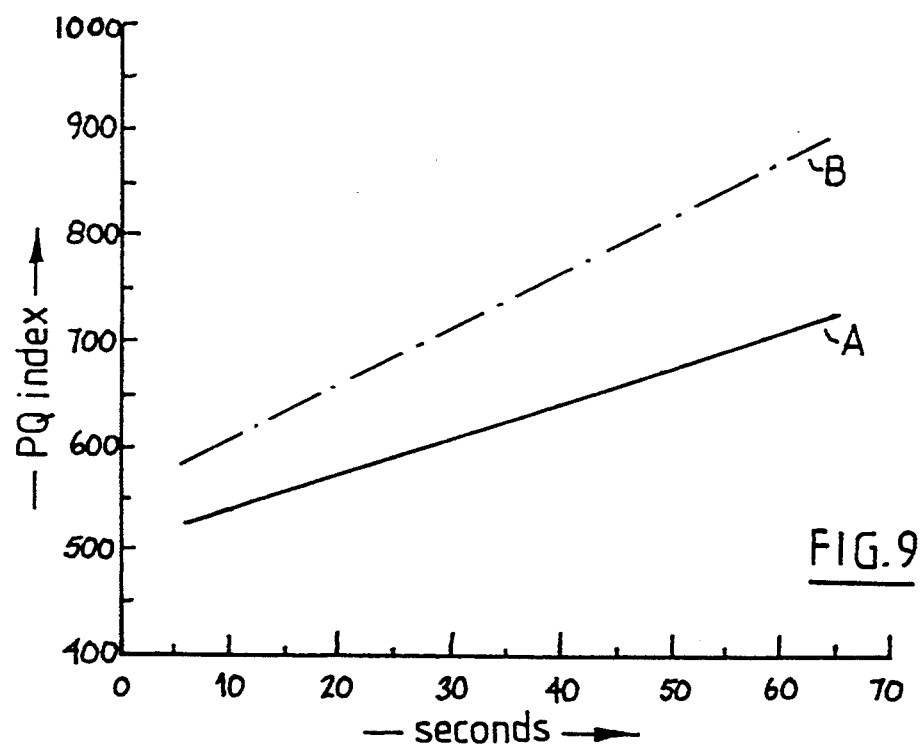

FIG. 8 shows how PQ readings taken on the device of FIG. 1 with a bottle containing a sample of a depth greater than 10 mm vary with time. Graph A in FIG. 8 is for a sample containing a particle burden of 30% w/w of non-spherical particles sized between 38 and 45 microns diameter and 70% w/w of spherical particles sized between 7 and 8 microns diameter. Graph B in FIG. 8 is for a sample containing a particle burden of 70% w/w of non-spherical particles sized between 38 and 45 microns diameter and 30% w/w of spherical particles sized between 7 and 8 microns diameter. It will be noted that in both cases a comparable long-term reading is obtained but that prior to reaching the long-term reading, the measured PQ value is sharply time dependent. FIG. 9 shows an expansion of the short time end of the graph of FIG. 8 showing that there is a more rapid settlement for the sample of graph B than for the sample of graph A. When graphs similar to those of FIGS. 8 and 9 are plotted for an oil of greater viscosity, the rate of increase in the short term (i.e. FIG. 9) goes inversely with increasing oil viscosity but the same long-term PQ value is secured for a comparable particle burden.

FIG. 9 illustrates a most important aspect of this invention allowing information on the particle size distribution in a burden to be determined by making a series of PQ readings as an agitated burden settles naturally under the influence of gravity.

Although use of a turntable to present samples to a sensing head is one convenient way of carrying out the method of the invention it is not the only way and, for example, bottles could be inserted one-by-one (e.g. manually) into a sensing cavity penetrated by the flux field of a sensing coil of a PQ measuring unit.

The simpler sampling method provided by this invention offers several advantages over the existing fixed volume pot method. Among these may be mentioned Higher sensitivity to ferromagnetic wear debris—a factor of ×3 has been recorded.

Good correlation with the known method—a coefficient of correlation of 0.92 has been recorded.

Faster measurements due to reduced sample handling.

Reliable and simple field measurements made by non-laboratory personnel—offering immediate decision making capability on site and associated cost savings.

The integrity of the sample is unaffected by the measurement, and the sample is unmodified and uncontaminated, so the actual sample measured can be retained in the bottle in which it was evaluated so that the bottle can be labelled for repeat measurements, checks or further evaluation.

The opportunity to obtain additional information concerning the particle size distribution of ferromagnetic debris within the sample in a bottle by noting the variation of PQ index with time is of considerable commercial value.

What is claimed is:

1. In a method of monitoring a sample of particle burdened lubricating oil taken from a use point of the oil to quantify the ferromagnetic particle burden contained therein, which method includes the steps of extracting a sample of oil with its particle burden from the use point of the oil, placing that sample in a container, creating a magnetic flux field using a sensing electromagnetic coil wherein said flux field extends to a determinable effective height above a container support, placing the container and its charge of oil on said container support in the magnetic flux field of the sensing electromagnetic coil, and noting the distortion of the flux field caused by the particle burden as a numerical Particle Quantifying (PQ) value, the improvement comprising the steps of determining said effective height of the flux field and filling said container to any depth in excess of said effective height of said flux field.

2. A method according to claim 1, wherein the use point is an oil-containing compartment of oil-lubricated equipment and the extraction of a sample is taken whilst the equipment is operating or immediately after it has ceased operating.

3. A method according to claim 2, wherein the sample is extracted using a suction sampling pump and is collected in the container which is placed in the flux field.

4. A method according to claim 3, wherein the suction sampling pump applies suction to the downstream end of a length of plastics tube contained in a screw-capped sample bottle threaded onto the pump body, the upstream end of said length being passed into the oil-containing compartment so that the extracted oil sample is transferred directly from the compartment to the bottle along the tube without contacting the pump.

5. A method according to claim 1, wherein the material of the container does not affect the flux field to any significant extent.

6. A method according to claim 1, wherein a plurality of numerical PQ values are taken on a sample in a given container to evaluate a rate of increase in PQ value with time.

7. A method of monitoring a sample of particle burdened lubricating oil taken from a use point of the oil to quantify the ferromagnetic particle burden contained therein, comprising the steps of;

creating a magnetic flux field using a sensing electromagnetic coil, wherein said flux field extends to a determinable effective height above a container support, determining the effective height of the flux field, providing a container made of a material which does not affect the flux field to any significant extent, marking the container at a container depth equivalent to the effective height of the flux field when the container is placed on the container support, extracting a sample of oil with its particle burden from the use point of the oil directly into the marked container to fill said container to any level above the mark placed thereon, placing the container and its charge of oil on said container support in the magnetic flux field of the sensing electromagnetic coil, and noting the distortion of the flux field caused by the particle burden as a Particle Quantifying (PQ) value.

* * * * *